United States Patent [19]

vonBebenburg et al.

[11] 4,073,792
[45] Feb. 14, 1978

[54] 5-ARYL-PYRIDO-(b-6,7)-1,4-DIAZAEPINE WITH AN ADDITIONAL FUSED HETEROCYCLIC RING

[75] Inventors: Walter vonBebenburg, Buchschlag; Heribert Offermanns, Grossauheim, both of Germany

[73] Assignee: Deutsche Gold- und Silber-Scheideanstalt Vormals Roessler, Frankfurt, Germany

[21] Appl. No.: 459,371

[22] Filed: Apr. 9, 1974

[30] Foreign Application Priority Data

Apr. 12, 1973 Austria .................. 3241/73

[51] Int. Cl.² .................. A61K 31/55; A61K 31/625; C07D 471/14
[52] U.S. Cl. .................. 260/296 H; 260/67.6 R; 260/239.3 B; 260/294.8 C; 424/232; 424/263
[58] Field of Search .................. 260/296 H

[56] References Cited

U.S. PATENT DOCUMENTS 3,314,941   4/1967   Littell .................. 260/239.3 B

OTHER PUBLICATIONS

Hester et al., J. Med. Chem., vol. 14, pp. 1078–1081 (1971).

*Primary Examiner*—Alton D. Rollins
*Attorney, Agent, or Firm*—Cushman, Darby & Cushman

[57] ABSTRACT

Compounds are prepared having the formula:

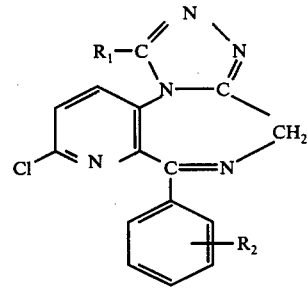

where $R_1$ is alkyl of 1 to 6 carbon atoms or phenyl and $R_2$ is hydrogen or halogen and tautomeric form and pharmacologically acceptable salts thereof. The compounds have sedative, psychosedative, anxiolytic and spasmolytic properties and in some cases antiphlogistic properties.

6 Claims, No Drawings

5-ARYL-PYRIDO-(b-6,7)-1,4-DIAZAEPINE WITH AN ADDITIONAL FUSED HETEROCYCLIC RING

The present invention is directed to new 5-aryl-pyrido-(b,6,7)-1,4-diazepines of the formula:

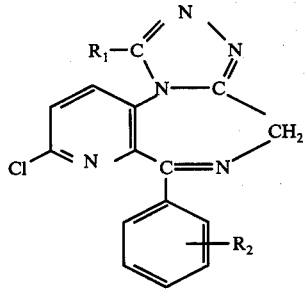

where $R_1$ is an alkyl group of 1 to 6 carbon atoms or phenyl and $R_2$ is hydrogen or halogen or their tautomeric form of their pharmacologically acceptable salts.

As the halogen atoms there are for example used halogens of atomic weight 19 to 80, i.e., chlorine, fluorine or bromine, especially chlorine or fluorine. As the above-named lower alkyl groups there are preferably present alkyl groups of 1 to 4 carbon atoms, especially 2 or 3 carbon atoms, examples of these are methyl, ethyl, isopropyl, butyl, sec. butyl, tert. butyl, amyl, hexyl and isobutyl. The compounds of formula I can also be present in the tautomeric form wherein a hydrogen of the diazepine —CH$_2$— group is transferred to the nitrogen in the 3-position or the nitrogen in the 6-position with a corresponding shift of the double bonds. The compounds in these cases can be present entirely or partially in one of the possible tautomeric forms. Generally, under the normal operating and storage conditions, an equilibrium is present.

In addition to the compounds mentioned in the working examples there are also included within the invention for example,
1-methyl-4H-6-o-chlorophenyl-8-s-triazolo-(4,3-a)-pyrido-(2,3-f)-1,4-diazepine;
1-methyl-4H-6-o-fluorophenyl-8-chloro-s-triazolo-(4,3-a)-pyrido-(2,3-f)-1,4-diazepine;
1-methyl-4H-6-p-fluorophenyl-8-chloro-s-triazolo-(4,3-a)-pyrido-(2,3-f-1,4-diazepine;
1-methyl-4H-6-o-bromophenyl-8-chloro-s-triazolo-(4,3-f)-1,4-diazepine;
1-methyl-4H-6-m-chlorophenyl-8-chloro-s-triazolo-(4,3-a)-pyrido-(2,3-f)-1,4-diazepine;
1-methyl-4H-6-p-chlorophenyl-8-chloro-s-triazolo-(4,3-a)-pyrido-(2,3-f)-1,4-diazepine;
1-phenyl-4H-6-o-chlorophenyl-8-chloro-s-triazolo-(4,3-a)-pyrido-(2,3-f)-1,4-diazepine;
1-phenyl-4H-6-o-fluorophenyl-8-chloro-s-triazolo-(4,3-a)-pyrido-(2,3-f)-1,4-diazepine;
1-ethyl-4H-6-phenyl-8-chloro-s-triazolo-(4,3-a)-pyrido-(2,3-f)-1,4-diazepine;
1-propyl-4H-6-phenyl-8-chloro-s-triazolo-(4,3-a)-pyrido-(2,3-f)-1,4-diazepine;
1-isopropyl-4H-6-phenyl-8-chloro-s-triazolo-(4,3-a)-pyrido-(2,3-f)-1,4-diazepine;
1-butyl-4H-6-phenyl-8-chloro-s-triazolo-(4,3-a)-pyrido-(2,3-f)-1,4-diazepine;
1-t-butyl-4-H-6-phenyl-8-chloro-s-triazolo-(4,3-a)-pyrido-(2,3-f)-1,4-diazepine;
1-hexyl-4H-6-phenyl-8-chloro-s-triazolo-(4,3-a)-pyrido-(2,3-f)-1,4-diazepine;
1-ethyl-4H-6-o-chlorophenyl-8-chloro-s-triazolo-(4,3-a)-pyrido-(2,3-f)-1,4-diazepine;
1-propyl-4H-6-o-fluorophenyl-8-chloro-s-triazolo-(4,3-a)-pyrido-(2,3-f)-1,4-diazepine;
1-t-butyl-4H-6-o-chlorophenyl-8-chloro-s-triazolo-(4,3-a)-pyrido-(2,3-f)-1,4-diazepine;
1-hexyl-4H-6-o-fluorophenyl-8-chloro-s-triazolo-(4,3-a)-pyrido-(2,3-f)-1,4-diazepine.

The compounds of the invention have valuable pharmacodynamic properties. They especially have sedative and marked psychosedative, anxiolytic (tranquilizing) and spasmolytic properties. Some of the compounds also have antiphlogistic properties.

The compounds of the invention can be prepared by a method which is known in itself by reacting a compound of the formula:

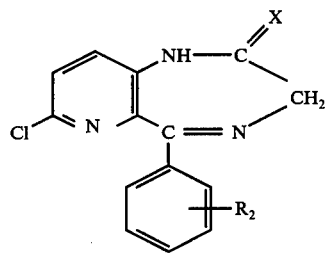

wherein $R_2$ is defined as above, and X is oxygen, sulfur, NH-, a benzylimino or in the tautomeric form is an alkylthio- or alkoxy group with 1 to 5 carbon atoms or is an alkyl- or dialkylamino group with alkyl radicals of 1 to 6 carbon atoms with a compound of the formula:

$$H_2N-NH-COR_1 \qquad III$$

wherein $R_1$ is as defined above and either simultaneously or subsequently cyclizing to a compound of formula I.

Compounds within Formula III include acetyl hydrazine, (acetyl hydrazide), propionyl hydrazide, butyryl hydrazide, isobutyryl hydrazide, valeroyl hydrazide, pivaloyl hydrazide, enanthoyl hydrazide.

The process for preparing the compounds of Formula I can be carried out in the melt or in a solvent or suspension agent at temperatures between 0° and 250° C., preferably 50° to 160° C. As solvents or suspension agents there can be used for example glacial acetic acid, aliphatic alcohols, e.g., methanol, ethanol, propanol, isopropanol, butanol, pentanol and hexanol; cycloalkanols, e.g., cyclohexanol, dioxane tetrahydrofurane, dimethyl sulfoxide, aliphatic ethers, e.g., diethyl ether, dipropyl ether, dimethyl formamide, chloroform, hydrocarbons such as toluene, xylene and benzene, chlorohydrocarbons, e.g., chlorobenzene, ether like solvents such as diethylene glycol dimethyl ether (diglyme) or diethylene glycol diethyl ether or amides such as N,N,N',N',N'',N''-hexamethyl phosphoric acid triamide. In a given case there can be added condensation agents such as polyphosphoric acid, polyphosphoric acid esters, e.g. the methyl, ethyl and butyl esters, sulfuric acid, zinc chloride, pyridine, pyridine salts, e.g., pyridine hydrochloride or tertiary amines, e.g., triethyl amine, tributyl amine and N,N-dimethyl aniline.

In case X in formula II designates an alkylthio group, an alkoxy group or a dialkylamino group, the compound of formula II is present in the tautomeric form which is based on the structure:

$$\begin{matrix} & XH \\ & | \\ -N & =C- \end{matrix}$$

Corresponding tautomeric forms or tautomeric equilibria can also be present for the remaining definitions of X. This is without significance for the reaction according to the process. As lower alkylthio or alkoxy groups X is preferably methylthio or ethylthio or methoxy or ethoxy. These groups can be activated by a substituent. Such activating groups are for example the o- or p-nitrobenzylthio or the o- or p-nitrobenzyloxy groups. As monosubstituted amino groups X is especially a lower alkylamino group such as the methylamino group or the ethylamino group or an aralkylamino group as the benzylamino group. As disubstituted amino grops X is especially a lower dialkylamino group such as the dimethylamino group and the diethylamino group.

Basic compounds of Formula I can be converted into their salts by conventional methods. As anions for these salts there can be employed the known and therapeutically usable (pharmacologically acceptable) acid residues. For example, there can be used acids such as sulfuric acid, phosphoric acid, hydrohalic acids, e.g., hydrochloric acid or hydrobromic acid, ethylenediamine tetraacetic acid, sulfamic acid, benzene sulfonic acid, p-toluene sulfonic acid, camphor sulfonic acid, methane sulfonic acid, guarazulene sulfonic acid, maleic acid, fumaric acid, oxalic acid, tartaric acid, lactic acid, citric acid, ascorbic acid, glyconic acid, salicyclic acid, acetic acid, propionic acid, gluconic acid, benzoic acid, acetamidoacetic acid, hydroxyethane sulfonic acid, malonic acid.

The free bases can be produced again from the salts of the compounds in customary manner, for example, by treatment of a solution in an organic medium, such as alcohols (e.g., methanol, ethanol or isopropanol) with soda or soda lye (caustic soda solution).

Those compounds of formula I which contain asymmetrical carbon atoms and as a result are racemates, can be split into the optically active isomers in known manner with the help of an optically active acid. However, it is also possible to employ from the beginning an optically active or diastereomeric form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, cremes, powders, liquids, dusts or aerosols. As liquids there can be used for example, oily or aqueous solutions or suspensions, emulsions, injectable aqueous and oily solutions or suspensions.

The starting compounds used in the process, e.g., those of formula II can be prepared for example according to the process of von Bebenburg et al U.S. application Ser. No. 313,542 filed Dec. 8, 1972 or in analogous manner to that process. The entire disclosure of the von Bebenburg et al. U.S. application is hereby incorporated by reference. The compounds of formula II are claimed as new compounds in said von Bebenburg et al application. While said von Bebenburg et al. application is now abandoned a continuation-in-part Ser. No. 507,605 filed Sept. 19, 1974 has now issued into U.S. Pat. No. 4,008,223.

As explained above, examples of compounds within the present invention having formula I are those where $R_1$ is an alkyl group with 1 to 6 carbon atoms while $R_2$ is hydrogen or compounds in which in formula I $R_1$ is an alkyl group of 1 to 6 carbon atoms and $R_2$ is chlorine or fluorine or compounds in which $R_1$ is a phenyl group and $R_2$ is chlorine or fluorine.

Unless otherwise indicated, all parts and percentages are by weight.

EXAMPLE 1

1-methyl-4H-6-phenyl-8-chloro-s-triazolo-(4,3-a)-pyrido-(2,3-f)-1,4-diazepine

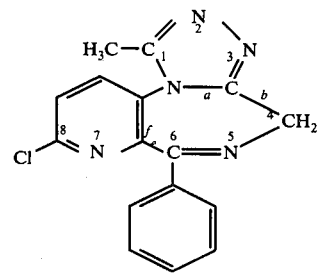

A mixture of 6 grams of acetyl hydrazine, 10 grams of 5-phenyl-6-aza-7-chloro-1,2-dihydro-3H-1,4-benzodiazepinthione-(2) and 50 ml of dioxane were heated for 20 minutes at 50° to 60° C. The compound crystallizing out was filtered off with suction after cooling (in a given case it can be recrystallized from ethanol) and subsequently heated for 30 minutes in 40 ml of n-hexanol to 140° to 150° C. After cooling the substance crystallized out. It was recrystallized from hexanol. M.P. 258° to 260° C.; Yield 3.5 grams.

The starting material of formula II was produced as set forth in Example 25 of the aforementioned von Bebenburg et al Application Ser. No. 313,543 as follows:

A mixture of 54 grams of 5-phenyl-6-aza-7-chloro-1,2-dihydro-3H-1,4-benzodiazepinone-(2), 44 grams of phosphorus pentasulfide and 600 ml toluene were boiled at reflux for 2.5 hours under nitrogen. The granular precipitate was filtered off with suction, agitated several times with chloroform, subsequently treated with aqueous ammonia and extracted once again with chloroform. After drying the thione was crystallized out in pure form from the extract. Yield 30 grams; M.P. 202° C. The preparation of 5-phenyl-6-aza-7-chloro-1,2-dihydro-3H-1,4-benzodiazepinone-(2) is described in Examples 1 and 2 of the aforementioned von Bebenburg et al application Ser. No. 313,542.

EXAMPLE 2

1,6-diphenyl-8-chloro-s-triazolo-(4,3-a)-pyrido-(2,3-f)-4H-1,4-diazepine:

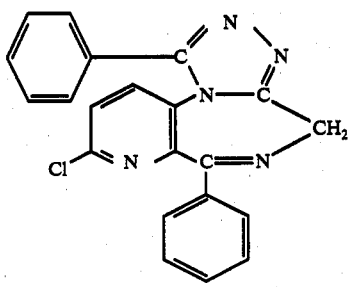

A mixture of 9 grams of 5-phenyl-6-aza-7-chloro-1,2-dihydro-3H-1,4-benzodiazepinthione-(2), 10 grams of N-benzoyl hydrazide and 60 ml of dioxane were heated on the water bath for 45 minutes with stirring. After some time the 2-[2-benzoylhydrazino-(1)]-5-phenyl-6-aza-7-chloro-3H-1,4-benzodiazepine began to crystallize out. After cooling it was filtered off with suction and thoroughly washed with alcohol and ether. Yield 12 grams; M.P. 193° C.

11 grams of this material were boiled for 90 minutes under reflux in 80 ml of n-hexanol. After cooling the title substance which crystallized out was filtered off with suction and recrystallized from ethanol. M.P. 246° C.; Yield 5.5 grams.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers amd assistants as set forth for example are those recommended in the following literature ad adjuvants for pharmacy, cosmetic and related fields such as in Ullmann's *Encyklopaedie der technischen Chemie*, Vol. 4 (1953), pages 1–39; *Journal of Pharmaceutical Sciences*, Vol. 52 (1963), pages 918 et seq.; H.v. Czetsch-Lindenwald, *Hilfstoffe fur Pharmazie und angrenzende Gebiete; Pharm. Ind.* Vol. 2 (1961), pages 72 et seq.; Dr. H. P. Fiedler, *Lexikon der Hilfstoffe fur Pharmazie, Kosmetik und angrenzende Gebiete*, Cantor Kg. Aulendorf i. Wurtt, 1971.

Examples of such materials include gelatin, natural sugars such as sucrose or lactose, lecithin, pectin, starch (for example corn starch), tylose, talc lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols, (for example, methyl hydroxypropyl cellulose, methyl cellulose, hydroxyethyl cellulose), stearates, e.g., methylstearate, and glyceryl stearate, magnesium and calcium salts of fatty acids with 12 to 22 carbon atoms, expecially saturated acids (for example calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, glycol furfural, dimethyl acetamide, lactamide, lactates, e.g., ethyl lactate, ethyl carbonate, silicones (especially middle viscosity dimethyl polysiloxane) and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., monoacetic diacetin, glyceryl monostearate, glyceryl distearate, glyceryl monopalmitate, paraffins and the like.

In the production of the preparations there can be used known and conventional solvent aids. As solvent aids there can be used, for example, polyoxyethylated fats, e.g., polyoxyethylated oleo triglyceride, linolized oleotriglyceride. Examples of oleotriglycerides are olive oil, peanut oil, castor oil, sesame oil, cottonseed oil, corn oil (see also Dr. H. P. Fiedler, *Lexikon der Hilfsstoffe fur Pharmazie, Kosmetik und angrenzende Gebiete*, 1971, pages 191 to 195).

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Furthermore, there can be added preservatives, stabilizers, buffers, taste correctives, antioxidants and complex formers (for example ethylenediamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used, for example, sodium meta-bisulfite, ascorbic acid, gallic acid, alkyl gallates, e.g., methyl gallate and ethyl gallate, butyl hydroxyanisole, nordihydroguararetic acid, tocopherols such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example, lower alkyl esters such as the methyl ester and the ethyl ester benzoic acid), sodium benzoate, trichloroisobutyl alcohol, phenol cresol, benzethonium chloride and formalin derivatives).

The pharmacological and galenical treatment of the compounds of the invention takes place according to the usual standard methods. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The drugs can be used for example orally, parenterally, rectally, vaginally, perlingually or locally.

It is also possible to add other medicines.

The compounds of the invention show a good anticonvulsive or anxiolytic effect and/or a sedative effect in the cardiazole shock test (mouse), in the spasmolytic test of Tedeschi (mouse) as well as in the motility test (mouse) in the circular cage of F. Heim.

This activity is comparable to the activity of known medicine chlorodiazepoxide.

The lowest effective dosage in the above-mentioned animal experiments is for example 0.5 mg/kg body weight orally, 0.1 mg/kg body weight intravenously and 0.2 mg/kg sublinqually.

As general dosage ranges there can be used 0.5 to 20 mg/kg body weight orally, 0.1 to 4 mg/kg body weight intravenously and 0.2–8 mg/kg sublinqually.

The compounds of the invention are useful in treating anxiety, stress and restless conditions, vegetative dystony, nervousness, irritation, volatile moods, footlight fever (e.g., for actors), weather feeling (i.e., body reactions to impending weather changes), behavior and adaption disturbances of children. The compounds are also useful in functional cardio-vascular, gastrointestinal and respiratory problems and in menstrual and climatic disturbances as well as in preoperative interferences and in assisting births.

The pharmaceutical preparations frequently contain between 1 and 10% of the active component (or components) of the invention.

The compounds can be delivered in the form of tablets, capsules, pills, dragees, suppositories, slaves, gels, creams, powders, liquids, dusts or areosols. As liquids there can be used oily or aqueous solutions or suspensions, emulsions; the preferred forms of use are as tablets which contain between 5 and 50 mg of active material of solutions which contain between 0.1 and 1% of active material.

In individual doses the amount of active component of the invention can be used for example in an amount of:

(a) in oral dispensation between 1 and 50 mg, (b) in parenteral dispensation (for example, intravenously, intramuscularly) between 0.1 and 10 mg, (c) in inhalation dispensation (solutions or aerosols) between 0.2 and 20 mg., (d) in rectal or vaginal dispensation between 0.2 and 20 mg.

(The dosages in each case are based on the free base).

For example, there is recommended the use of 3 tablets containing 1 to 50 mg of active ingredient 3 times daily or for example intravenously the injection 1 to 3 times daily of a 0.5 to 2 ml ampoule containing 0.1 to 10 mg of active substance. In oral preparations the minimum daily dosage for example is 1.0 mg; the maximum daily dosage should not be over 150 mg.

In the treatment of dogs and cats the oral individual dosage in general is between about 0.5 and 50 mg/kg body weight; the parenteral individual dosage is between about 0.1 and 10 mg/kg body weight. In the treatment of horses and cattle the individual dosage orally is generally between 1 and 200 mg/kg; the parenteral individual dosage is between 0.1 and 50 mg/kg body weight.

The acute toxicity of the compounds of the invention in the mouse (expressed by the $LD_{50}$ mg/kg method of Miller and Tainter, *Proc. Soc. Exper. Biol. and Med.*, Vol. 57 (1944) pages 261 et seq.) in oral application is between 200 and 2000 mg/kg (or above 2000 mg/kg).

The drugs can be used in human medicine, in veterinary medicine, e.g., to treat cats, dogs, horses, sheep, cattle, goats and pigs or in agriculture. The drugs can be used alone or in admixture with other pharmacologically active materials.

The salts can also be used as curing agents for melamine-formaldehyde resins.

What is claimed is:

1. A 5-arylpyrido-(b,6,7)-1,4-diazepine of the formula:

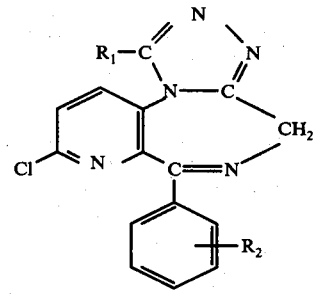

where $R_1$ is an alkyl group of 1 to 6 carbon atoms and $R_2$ is hydrogen or halogen of atomic weight 19 to 80 or the tautomeric form thereof or a pharmacologically acceptable salt thereof.

2. A compound according to claim 1, wherein $R_1$ is alkyl of 1 to 4 carbon atoms.

3. A compound according to claim 2 wherein $R_2$ is hydrogen.

4. A compound according to claim 3 wherein $R_1$ is methyl.

5. A compound to claim 3 wherein $R_1$ is alkyl of 2 to 3 carbon atoms.

6. A compound according to claim 2 wherein $R_2$ is chlorine or fluorine.

* * * * *